United States Patent [19]
Sheridan et al.

[11] Patent Number: 5,627,328
[45] Date of Patent: May 6, 1997

[54] GAS SAMPLING SYSTEM AND METHOD

[75] Inventors: David R. Sheridan, Menlo Park; Glenn C. Morrison, Berkeley, both of Calif.

[73] Assignee: Gas Research Institute, Chicago, Ill.

[21] Appl. No.: 580,574

[22] Filed: Dec. 29, 1995

[51] Int. Cl.$^6$ .................................................. G01N 1/24
[52] U.S. Cl. .................................................. 73/863.83
[58] Field of Search ........................... 73/1 G, 23.31, 73/863.01, 863.21, 863.23, 863.24, 863.31, 863.81, 863.83, 864.34, 864.73, 864.81

[56] References Cited

U.S. PATENT DOCUMENTS

| | | | |
|---|---|---|---|
| 4,094,187 | 6/1978 | Navarre, Jr. | 73/864.34 |
| 4,134,289 | 1/1979 | Bohl et al. | 73/864.34 |
| 4,738,147 | 4/1988 | Tomlin | 73/864 |
| 4,974,455 | 12/1990 | McGowan et al. | 73/863 |
| 5,178,022 | 1/1993 | Tomlin . | |
| 5,209,102 | 5/1993 | Wang et al. . | |
| 5,237,881 | 8/1993 | Ross | 73/863 |
| 5,423,228 | 6/1995 | Budd et al. | 73/863 |
| 5,473,951 | 12/1995 | Tomlin . | |

*Primary Examiner*—Robert Raevis
*Attorney, Agent, or Firm*—Thomas, Kayden, Horstemeyer & Risley

[57] ABSTRACT

A gas sampling system and method that utilizes a double aspirator design to precisely control the flow rate of a gas sample past a sensor (44, 46, or 48). The double aspirator design includes a primary aspirator (24) to draw a gas sample from the exhaust stack (14) at a first flow rate and a secondary aspirator (26) to draw a portion of the gas sample from the primary aspirator at a second flow rate past the sensors. In addition, a first pressure sensor (74) and second pressure sensor (76) are provided in order to monitor changes in the pressure differential across the sensor so that corresponding changes in the second flow rate can be accounted for by the control unit (18) when processing the measurement data from the sensor.

17 Claims, 2 Drawing Sheets

GAS SAMPLING SYSTEM AND METHOD

FIELD OF THE INVENTION

This invention generally relates to an emissions monitoring system for analyzing the components of a gas sample extracted from a gas stream in an exhaust stack of an industrial process, and more particularly, to a system and method that utilizes a double aspirator design in order to precisely control the flow rate of a gas sample past a sensor of an emissions monitoring system.

BACKGROUND OF THE INVENTION

Beginning around the time of the industrial revolution, a time when industrial process facilities were cropping up one after another, unhealthy levels of hazardous pollutants began being discharged into the environment by these industrial processing facilities. As the number of industrial processing facilities has continued to grow over the years, particularly within small geographic pockets around the country, the problem only worsened. Particularly, the discharge of pollutant gases into the atmosphere, has been linked with numerous diseases and has allegedly contributed to the formation of ozone and smog.

Since the time of the industrial revolution, as the deterioration of the environment due to process emissions became more evident and public concern became greater, the government has implemented legislation at the federal, state, and local levels in order to both monitor and reduce the number of pollutants released into the environment. Most notably, in 1970, the Environmental Protection Agency (EPA) was formed by President Nixon and significant amendments were made to the Clean Air Act. Since the Clean Air Act Amendments of 1970, numerous other amendments have been made to the Clean Air Act in efforts to further air quality standards.

As a result, virtually all large scale industrial processes in the United States are required by law to monitor their emissions on a continuous basis to ensure their compliance with emission levels of particular pollutants as set by a local regulatory agency, typically an arm of a state's EPA. This often requires the process facility to perform continuous monitoring of their emissions to avoid substantial frees and/or criminal prosecution. In order to perform these compliance measurements, many continuous emissions monitors (CEMs) have been developed to analyze the contents of the emissions of an industrial process facility.

Typically, CEMs comprise laboratory-type instruments which use analytical methods to determine the concentration of particular pollutants contained in a gas sample extracted from an emission stream of a process. These instruments are relatively expensive and complex, but are utilized because they are capable of providing the high level of accuracy required by the EPA. These instruments use a variety of known sensing methodologies to sense a target gas. For instance, non-dispersive infrared (NDIR) analyzers are used to measure carbon monoxide (CO). As another example, chemiluminescence analyzers are used to measure nitrogen oxides (i.e., NO or $NO_2$, referred to generically hereinafter as $NO_x$. However, because these instruments operate at room temperature and, by their nature, are sensitive to external factors, they must be remotely located with respect to the exhaust stack at a remote monitoring facility. Consequently, the gas sample that is extracted from the exhaust stack is delivered to the remote monitoring facility by a sample line that typically ranges in length between 200 to 1,000 feet. Moreover, the sample line is heated in order to prevent condensation of the water vapor, (generated by the combustion process), within the gas sample because the water condensation can combine with the acid gases in the exhaust (i.e., $NO_x$ and $SO_x$), to form corrosive acids that may damage the sample line and the monitoring instruments. Water condensation also serves to partially scrub the $NO_x$ from the sample gas causing the monitoring instruments to read $NO_x$ at a falsely low level. Alternatively, in order to reduce and/or prevent water condensation, the sample gas can be diluted with instrument quality air at the probe using a dilution probe to decrease the water vapor concentration to a level where the water remains a vapor at ambient temperatures, and thus, alleviating the need for a heated sample line.

Further, the instruments typically require a dry gas sample. Consequently, a water knock-out system (i.e., condenser) must be provided at the monitoring facility so that any moisture in the gas sample is removed before the measurements are taken. In this regard, dilution probe systems have been found to be sufficient in reducing the water vapor in the gas sample to acceptable levels. However, dilution probes are costly and dilute the target gases to levels that require instruments with even greater relative sensitivity. Lastly, the combination of the long sample lines and the water knock-out or dilution probes systems, the volume of sample gas that must be displaced (referred to as dead volume) during measurement is considerable, generally taking the instrument more than 60 seconds to respond to changing levels of the target at the exhaust stack.

Accordingly, because these instruments must be located in a remote monitoring facility, require a heated sample line and a conditioning system to remove water vapor, the installation and maintenance costs associated with such continuous emissions monitoring systems have been quite costly, typically in the range of $200,000–$500,000 for installation alone.

In addition to performing continuous emissions monitoring, many industrial processes benefit from monitoring emissions for control purposes. Particularly, in a process utilizing combustion, control over the efficiency of the combustion is of particular importance. For example, it is preferable to have as little excess air at the point of combustion so as to prevent heat transfer to the exhaust stream which results in heat loss. Thus, by measuring the amount of air (i.e., oxygen in an exhaust stream) the appropriate changes can be implemented in the process so that only a minimal amount of excess air is found in the exhaust stream.

As another example, the efficiency of $NO_x$ reduction schemes, such as steam injection, can be monitored by taking $NO_x$ measurements before and after the steam injection process. For example, the efficiency of a selective catalytic reduction (SCR) process can be improved by measuring the amount of $NO_x$ before, or upstream, the point at which the reducing gas (i.e., ammonia) is introduced so that the appropriate amount of reducing gas is provided. This prevents the introduction of excess reducing gas into the exhaust stream, resulting in the excess reducing gas being emitted into the environment which is both wasteful and may constitute a nuisance to the surrounding community.

In contrast to continuous emission monitoring, process control monitoring requires a much faster response time, typically on the order to 15–20 seconds for each gas measured. As mentioned above, CEMs typically require more than 60 seconds between reports because of the long sample lines and the nature of the instruments as described hereinbefore.

Further, process control monitoring does not require the level of accuracy that is required by the EPA in continues emissions monitoring systems. Particularly, process control monitoring does not require an absolute value of the amount of target gas in the exhaust stream, but alternatively, only tracks trending in the concentration levels of the particular gases. Consequently, process control monitoring is typically implemented using relatively inexpensive catalytic heat-flux sensors which have lower specificity than the measurement instruments associated with continuous emission monitoring systems. For instance, catalytic heat-flux sensors are only required to measure concentrations at or above levels of 100 parts per million (ppm). Whereas, continuous emission monitoring systems are typically required to measure levels below 100 ppm.

Yet another difference exists between continuous emissions monitoring and process control monitoring in the calibration scheme utilized by each. In process control monitoring where trends are monitored, calibration is performed approximately once every calendar quarter and only on the sensor devices. This calibration scheme is referred to as unit calibration. Conversely, in continuous emission monitoring where a high level of accuracy is required in the measurements, calibration is performed approximately once every day on the whole system, including the probe and sample lines. This calibration scheme is referred to as probe calibration. In probe calibration, the calibration gas is introduced to the monitoring system at the probe rather than at the sensors, as is the case with unit calibration.

Therefore, because of the differences in process control monitoring and continuous emissions monitoring, as delineated above, separate emissions monitoring systems, and particularly, separate gas sampling systems, have historically been used.

Hence, a heretofore unaddressed need exist in the industry for a gas sampling system and method that can measure emissions with accuracy, perform unit and probe calibration, and generate reports at intervals on the order of every 15–30 seconds per gas so as to be functional for operation in both process control monitoring and continuous emission monitoring.

SUMMARY OF THE INVENTION

An object of the present invention is to overcome the deficiencies and inadequacies in the prior art as described above and as generally known in the industry.

Another object of the present invention is to provide for both continuous emission monitoring and process control monitoring of the emissions of a process.

Another object of the present invention is to provide precise control over the flow rate of a gas sample past the sensors of an emissions monitoring system.

Another object of the present invention is to detect changes in the pressure differential across the sensors of an emissions measuring system in order that appropriate corrections can be made to the measured value by the monitoring system.

Another object of the present invention is to provide for both unit and probe calibration.

Briefly stated, the present invention is a gas sampling system for use in an emissions monitoring system for performing both continuous emission monitoring and process control monitoring. The gas sampling system of the present invention achieves this, in part, by providing precise control over the flow rate of the gas sample to a sensor army containing catalytic heat-flux sensor so as to increase the sensitivity (i.e., specificity) of the catalytic heat-flux sensors, enabling the sensors to measure emissions at lower levels and with greater accuracy. The improved flow control is provided in the present invention by the incorporation of a double aspirator configuration and by monitoring the pressure differential across the sensor array. The present invention further incorporates a calibration scheme capable of performing both unit and probe calibration. Accordingly, because of the improved flow control and calibration scheme of the present invention, the gas sampling system of the present invention can be utilized for both process control monitoring and continuous emission monitoring.

A gas sampling system in accordance with the present invention includes a primary aspirator for drawing a gas sample from the gas emission stream in an exhaust stack at a first flow rate. A secondary aspirator then draws a portion of the gas sample at the primary aspirator at a second flow rate which is less than the first flow rate. This double aspirator configuration allows for precise control of the second flow rate which is delivered to a sensor array that contains a sensor for each of the gases of interest, such as $NO_x$, CO, and $O_2$. The secondary aspirator is disposed downstream of the sensor array so the portion of the gas sample drawn from the primary is equally divided between the respective sensors.

A critical orifice is disposed immediately downstream of each respective sensor and is sized so that the vacuum created by the secondary aspirator causes the flow through each orifice to be critical. This prevents the flow rate of each gas sample passing each respective sensor from being affected by changes in pressure downstream of the critical orifice.

In addition, absolute pressure sensors are provided to measure the pressure upstream and downstream of the critical orifices (and therefore the sensor army) in order to monitor the pressure differential across the sensor array. Thus, if an unexpected change in the pressure differential across the sensor array is detected, such that the flow through the orifices is not critical, a system fault alarm will occur and/or appropriate corrections will be made in the processing of the measured value in order to account for the flow rate changes resulting from changes in the pressure differential.

A gas sampling system in accordance with the present invention further provides for both unit and probe calibration. Specifically, a three-way plug valve is fed by an input line coupled to one or more calibration gases that can be selectively introduced into the input line. The output of the valve is selectively coupled to either a first output line that deliver the calibration gas of choice directly to the sensor array, or alternatively, to a second output line that deliver the calibration gas of choice to a probe at the exhaust stack.

The present invention also provides for and can be conceptualized as a method for analyzing components of a gas sample extracted from a gas emission stream in an exhaust stack which comprises the following steps: drawing a gas sample from a gas stream in an exhaust stack at a first flow rate; drawing a first portion of the gas sample at a second flow rate that is less than the first flow rate; passing the first portion of the sample gas to a sensor array including at least two sensors in a parallel configuration so the gas sample is divided between the sensors of the sensor array; and desensitizing the flow rate of the gas sample through the sensor array to changes in downstream pressures by incorporating a critical orifice directly downstream of each respective sensor in the sensor array. An additional step that may be performed is measuring the pressure of the gas sample upstream and downstream of the sensor array in order to monitor changes in the pressure drop across the sensor army as a result of pressure changes.

An advantage of the gas sampling system in accordance with the present invention is that it can be configure in an on-stack or off-stack configuration without having to make adjustments to the system to account for the absence or presence of a pressure drop across the sample line. Specifically, the double aspirator design makes the flow rate of the gas sample at the sensor army less sensitive to changes in the pressure upstream of the primary vacuum device.

Other objects, features, and advantages of the present invention will become apparent to one skilled in the art upon examination of the following drawings and detailed description. It is intended that all such additional objects, features and advantages be included herein within the scope of the present invention, as defined by the appended claims.

BRIEF DESCRIPTION OF THE DRAWINGS

The present invention can be better understood with referenced to the following drawings. The elements of the drawings are not necessarily to scale, emphasis instead being placed upon clearly illustrating the principles of the present invention. Furthermore, like reference numerals designate corresponding parts throughout the several views.

DETAILED DESCRIPTION OF THE PREFERRED EMBODIMENT

1. System Overview

Figure 1A:
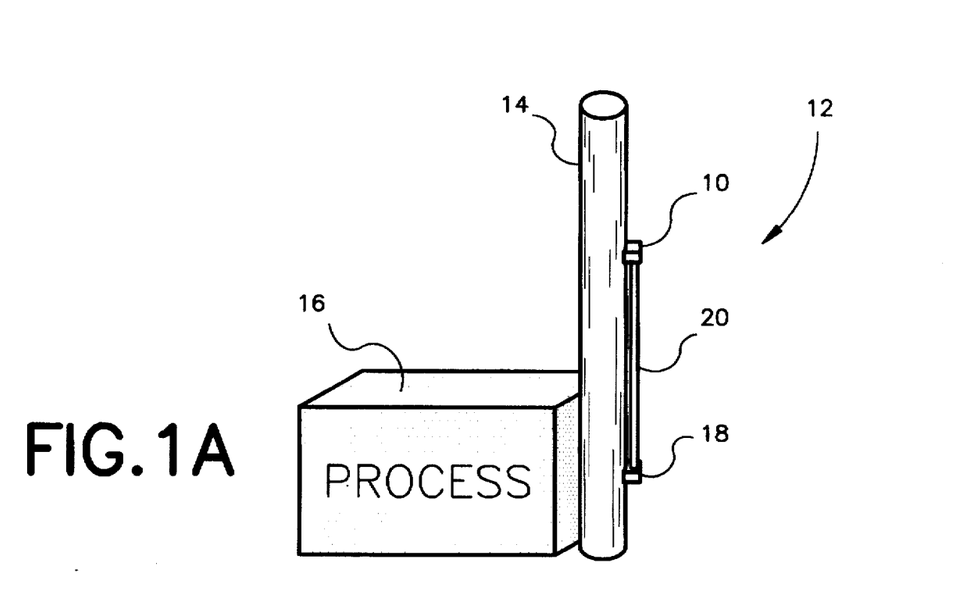
FIG. 1A is a schematic illustration of the present invention implemented in an on-stack configuration.

With reference to FIG. 1A, a gas sampling system 10 in accordance with the present invention is illustrated in an on-stack configuration of a gas monitoring system 12. The gas monitoring system 12 includes the gas sampling system 10 for extracting and measuring the concentration of particular gases in a gas emission stream in an exhaust stack 14 associated with a process facility 16, and a control unit 18 for receiving measurement signals from the gas sampling system 10 via cable 20 and for processing that information to determine measurement data.

The measurement data that is generated by the control unit 18 can be used for compliance measurement reporting as required by various federal, state, and/or local regulatory agencies, or for process control purposes in order to monitor the combustion efficiency of the process of process facility 16 and/or to evaluate the efficiency of a $NO_x$ reduction scheme, such as selective catalyst reduction. The data generated by control unit 18 can be displayed on a display device (not shown) such as a CRT or stored on a storage medium (not shown) such as a magnetic tape or floppy disk. Such a display device can be located at control unit 18, or preferably, located at a central control facility associated with the overall operation of process facility 16.

Figure 1B:
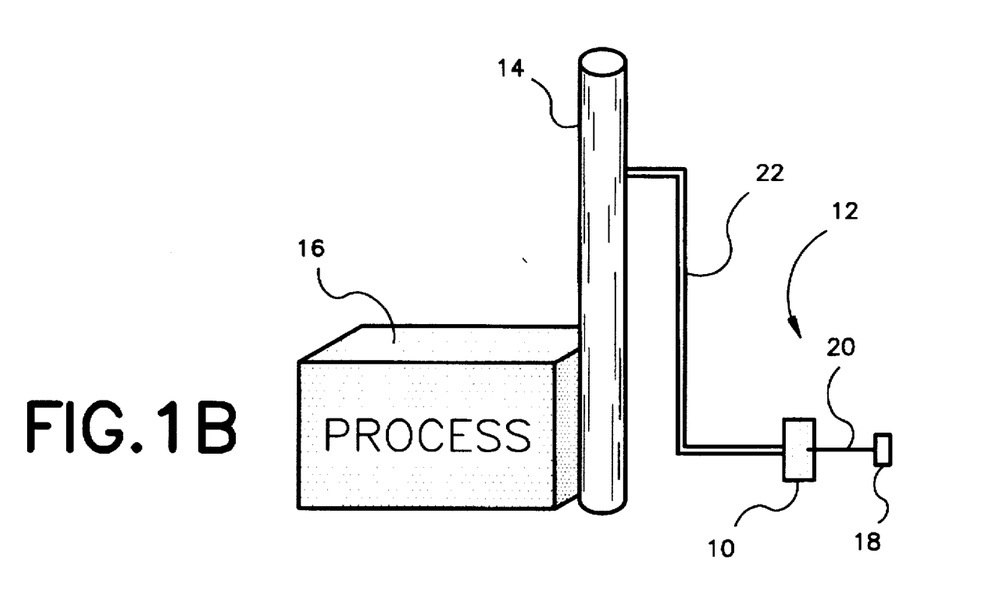
FIG. 1B is a schematic illustration of the present invention implemented in an off-stack configuration.

With reference to FIG. 1B, the gas sampling system 10 of gas monitoring system 12 is shown in an off-stack configuration. In the off-stack configuration, the gas sample extracted form exhaust stack 14 is delivered to the gas sampling system 10 by a sample line 22 which is generally heated. This configuration may be desirable in circumstances where the area around the exhaust stack 14 is considered hazardous or if it is too costly for a technician to perform maintenance operations at the exhaust stack 14.

Figure 2:
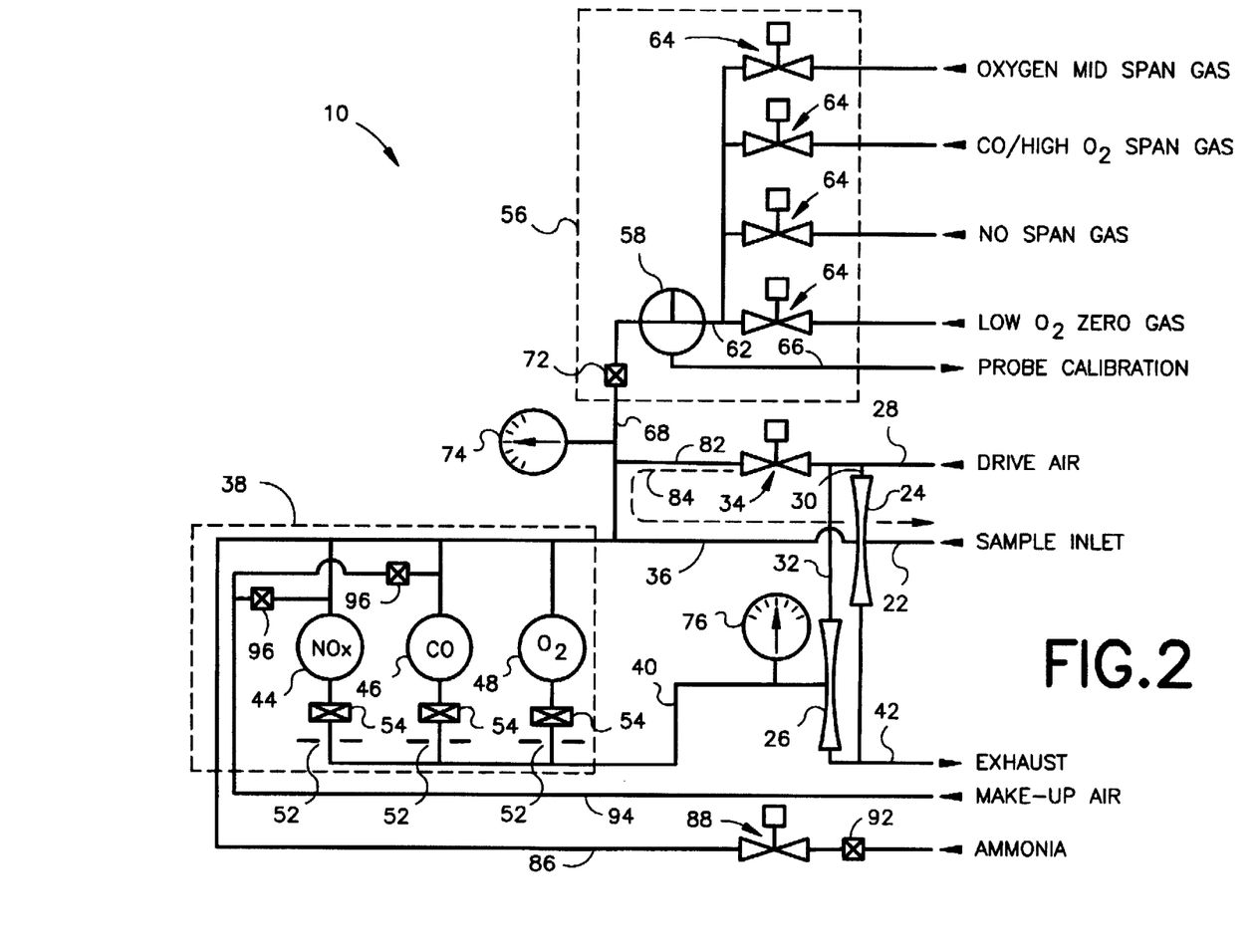
FIG. 2 is a flow diagram of the gas sampling system of the present invention as illustrated in FIGS. 1A and 1B.

With reference to FIG. 2, the functionality of the gas sampling system 10 will now be discussed in detail. It should be noted, however, that a gas sampling system 10 in accordance with the present invention can be implemented in numerous ways. The embodiment illustrated in FIG. 2 is merely one such implementation and numerous other implementations of the gas sampling system 10 will be obvious to one of ordinary skill in the art upon reading the present disclosure.

The gas sampling system 10 includes a primary aspirator 24 that pulls a gas sample from the exhaust stack 14 (FIGS. 1A and 1B) to the gas sampling system 10 via sample line 22. Preferably, the gas sample is drawn over sample line 22 at a flow rate of approximately 10 liters per minute. The gas sample may be extracted from the exhaust stack 14 by any of a variety of well-known methods, but preferably, utilizing a probe comprised of ⅜ inch pipe fitted with a sintered metal filter element at the pipe inlet. It is preferable that the average pore size of the filter element be 10 microns, the outer surface area of the filter be greater than 200 square centimeters, and the material of construction be 316L stainless steel. A suitable probe having the aforementioned configuration is Model 2200, manufactured by Mott Metallurgical Corporation, Conn., USA. A secondary aspirator 26, pulls a portion of the gas sample from the primary aspirator 24 at a slower flow rate than that of the gas in sample line 22. Preferably, the gas sample drawn by the secondary aspirator 26 is drawn at approximately 3 liters per minute.

In the preferred embodiment, the primary and secondary aspirators are eductors. The primary and secondary educators draw the gas sample with a vacuum created by passing pressurized (i.e., compressed) air through a restricted area such as a venturi. This produces a vacuum that is utilized to pull the gas sample toward the respective eductor. For instance, with reference to the primary eductor 24 in FIG. 2, compressed air, referred to as drive air, is provided over line 28 which branches off into lines 30, 32 so that the drive air is delivered to the primary eductor 24 and the secondary eductor 26, respectively. A normally closed blowback valve 34 is provided on line 28 downstream of the branch lines 30, 32, the operation of which is discussed below. As the pressurized air passes through the venturi of the primary eductor 24, a vacuum is created at the venturi. The sample line 22 is coupled to the primary eductor 24 downstream of the venturi so that the vacuum in the primary eductor 24 pulls the gas sample from the probe, through sample line 22, to the primary eductor 24. Preferably the gas sample in line 22 has a flow rate of approximately 10 liters per minute but this is difficult to control because changes in the process effect the air pressure in the exhaust stack 14, which likewise effects the flow rate of the gas sample in line 22. Note that the operation of educators, as generally described above, is well known in the industry.

The secondary aspirator 26 operates in substantially the same manner as described above with regard to the primary aspirator 24, as described above. The secondary aspirator 26 receives the drive air over line 32 which passes through the venturi of the secondary aspirator 26 so as to create a vacuum. Utilizing this vacuum, a portion of the gas sample at the primary eductor 24 is pulled at a precise flow rate over a secondary flow line 36, through a sensor army 38, and over another line 40 to the secondary aspirator 26. Preferably, the gas sample in line 36 has a flow rate of approximately 3 liters per minute. Thus, by precisely controlling the flow rate of the gas sample through the sensor array 38 via the double aspirator configuration of the present invention, the accuracy of the measurements taken by monitoring system 12 is improved.

At the secondary aspirator 26, the gas sample and drive air are combined and exhausted through line 42. Likewise, the remaining portion of the gas sample at the primary aspirator that is not pulled through the sensor array 38 is combined with the drive air in line 30 and exhausted through line 42.

The sensor army 38 comprises one or more sensors, each sensor being configured to measure the concentration of particular gas of interest. As shown in FIG. 2, a $NO_x$ sensor 44, a CO sensor 46, and a $O_2$ sensor 48 are provided in the sensor array 38. In the preferred embodiment, the $NO_x$ sensor 44 and the CO sensor 46 are the catalytic heat-flux Harsh Environment Sensors manufactured by Advance Sensor Devices, Inc., Mountain View, Calif., USA and commercially referred to as HES-$NO_x$ and HES-CO, respectively. In addition, the $O_2$ sensor 48 is preferably a zirconia-based sensor, such as the Oxygen Lambda sensor, manufactured by Robert Bosch Company, Gemany. Preferably, the sensors 44, 46, and 48 are configured in a parallel arrangement so that the gas sample in line 36 is equally divided between the respective sensors. For example, if the gas sample has a flow rate of 3 liters per minute in over line 36, equal portions of the gas sample will be delivered to each sensor at approximately 1 liter per minute. However, it should be noted that the amount and flow rate of the respective gas samples delivered to the various sensor need not be equal, merely constant. The operation of the respective sensors 44, 46, and 48 is discussed in detail below.

A critical orifice 52 is provided directly downstream of each of the respective sensors 44, 46, and 48. The critical orifices 52, are specifically sized approximately 0.012 inches in diameter in the preferred embodiment, so that the vacuum created by the secondary aspirator 26 causes the flow through each orifice to be critical. This ensures that pressure changes downstream of sensor army 38 will not affect the flow rate past each of the respective sensors. It should be noted that critical orifices are widely used and their operation well known in the industry. Associated with each critical orifice 52 is a falter element 54 so that the orifices 52 do not become blocked or damaged by particulate in the flow. Each filter element 54 is disposed upstream and adjacent to its corresponding orifice 52. As an example, a suitable filter element 54 comprises a 3/15 inch diameter, 1/15 inch thick sintered metal disk, preferably constructed out of 316L stainless steel, and having an average pore diameter of approximately 2 microns.

Downstream of the sensor array 38, the gas samples distributed to each of the respective sensors 44, 46, and 48 are recombined and delivered to secondary aspirator 26 via line 40. As mentioned above, the gas sample in line 40, the drive air in line 32, and the drive air and gas sample in line 30 are combined in exhaust line 42 which is plumbed back to the exhaust stack 14 or vented directly into the atmosphere.

One of the features of the gas sampling system 10 that enables both continuous emissions monitoring and process control monitoring is the ability to provide for both probe and unit calibration. Specifically, a gas calibration module 56 is provided and includes a 3-way plug valve 58, hereinafter referred to as the calibration valve 58. The calibration valve 58 includes an inlet line 62 that is connected to a plurality of calibration gases, for instance but not limited to, a low $O_2$ gas (i.e., zero gas), a NO span gas, a CO\high $O_2$ span gas, and an $O_2$ mid-span gas, as illustrated in FIG. 2. Each of the respective calibration gases is connected to inlet line 62 via respective solenoid valves 64. The solenoid valves 64 are selectively controlled by the user, typically via electrical control signals from the control unit 18 (FIGS. 1A and 1B) in order to deliver a particular calibration gas to the calibrator valve 58.

The calibration valve 58 is configured as a two-position valve capable of directing the calibration gas from inlet line 62 into either of a probe calibration line 66 or a unit calibration line 68. As shown in FIG. 2, the calibration gas is directed by calibration valve 58 to the unit calibration line 68 where it floods the secondary gas sample stream in line 36, and thus, the sensor army 38. A sintered metal flow restrictor 72 is provided on the unit calibration line 68 in order to control the flow therethrough. Alternatively, if calibration valve 58 were rotated 90 degrees clockwise, the calibration gas would be directed to the probe calibration line 66 which delivers the calibration gas to the probe so that the calibration gas is drawn by the primary aspirator through the probe and sample line 22 to the gas sampling system 10. Again, a flow restrictor (not shown) is provided at the probe to meter the flow of calibration gas in probe calibration line 66.

An advantage of the calibration scheme of the present invention, as described hereinabove, is that no valve is required to switch between the gas sample flow and the calibration gas flow as used in the prior art. Specifically, the prior art sampling devices typically include a valve, manually or automatically operated, for switching between sample gas and the calibration gas. Because the sample gas generally contains the acid gases ($NO_x$ and $SO_x$) which combine with moisture, also found in the sample gas, to produce a corrosive mixture, these valves have a reduced operating life. Thus, by avoiding the use of such a valve, the gas sampling system 10 requires less maintenance.

Yet another feature of the gas sampling system 10 that enables both continuous emissions monitoring and process control monitoring is the ability to monitor the flow rate of the gas sample through the sensor array 38. This feature allows the gas monitoring system 12 to make the appropriate changes in the processing of the gas measurement data delivered to the control unit 18 in order to compensate for changes in the flow rate through the sensor array 38. Specifically, a pressure sensor 74 takes measurements upstream of the critical orifices 52 on line 68 and a second pressure sensor 76 takes measurements downstream of the critical orifices 52 on line 40. Preferably, pressure sensors 74, 76 are electronic pressure transducers which output a voltage proportional to the pressure in the respective lines, as are commercially available and well known in the industry. The output voltages of pressure sensors 74, 76 are then sent to the control unit 18 for processing with the measurement dam from sensors 44, 46, and 48. Further, if the gas sample flow is impeded (e.g., from particulate settling on the sample probe) such that the flow through the orifices 52 is not critical, the associated change in the pressure drop across the sensor array 38 will be detected by pressure sensors 74, 76, causing a system fault alarm to occur.

Yet another feature of the present invention is the ability to remove particulate that settles and accumulates at the exterior of the sample probe. A blow-back system is provided to periodically clean the flow lines and probe with a blast of air. The blow back is performed by selectively energizing, and thereby opening, the normally closed solenoid valve 34 which allows the compressed drive air in line 28 to recirculate in an upstream direction through a blowback line 82, line 68, line 36, and sample line 22, as indicated by dashed line 84 in FIG. 2. The pressure of the drive air is substantially greater than that of the gas sample so that the drive air pushes back and purges the sample line 22 and probe of the exhaust gas sample with a burst of air that is sufficient to clear away most all residue particulate in the flow lines and on the probe.

To assist the operation of the $NO_x$ sensor 44, the gas sampling system 10 combines ammonia with the gas sample delivered to the sensor 44 in line 36. In order to operate the $NO_x$ sensor 44 of the preferred embodiment, a small amount of ammonia is introduced into the gas sample delivered to the $NO_x$ sensor 44 to ensure the reaction of the catalyst utilized with the $NO_x$ sensor 44, as discussed in detail in U.S. Pat. No. 5,314,828, entitled "$NO_x$ Sensor and Process for Detecting $NO_x$," and issued on May 24, 1995, the disclosure of which is incorporated herein by reference as if set forth in full. Accordingly, the present invention provides anhydrous ammonia over line 86 which combines with the gas sample in line 36 at $NO_x$ sensor 44. A solenoid valve 88 on line 86 selectively opens and closes the ammonia source and a flow restrictor 92 meters the amount of ammonia provided to the $NO_x$ sensor 44. Preferably, the anhydrous ammonia in line 86 has a flow rate of 0.001 liters per minute.

Further, as required for the operation of the catalytic heat-flux sensors 44, 46 of the preferred embodiment, a small amount of excess oxygen is blended with the gas sample delivered to each of sensors 44, 46. In addition, because some processes operate at stoichiometric or rich conditions, a small amount of excess oxygen, referred to hereinafter as makeup air, is blended with the gas sample delivered to sensors 44, 46 in order to ensure proper sensor operation under all conditions. The makeup air is provided to sensors 44, 46 over line 94 which branches into two lines that are respectively coupled to the flow streams of the sensors 44 and 46. A flow restrictor 96 is provided on each branch of line 94 in order to meter the amount of makeup air provided to the respective sensors 44, 46. Preferably, the makeup air in line 94 has a flow rate of 0.1 liters per minute. The makeup air should be instrument quality air since any residual hydrocarbons in the airstream may be an interferant to the $NO_x$ and CO measurement indicators.

In construction, the gas sampling system 10 preferable comprises a modular design, whereby each module is machined out of 300 series stainless steel and integrated into one structure to form the gas sampling system 10. The gas sampling system 10 preferably includes a sensor module, a calibration module, and a aspirator module. The sensor module includes all the wearable parts such as the sensors 44, 46, and 48, filter elements 54, and critical orifices 52 so that these parts can be easily repaired or replaced by removing a single module. The calibration module includes the calibration valve 58 and flow restrictor 72. Lastly, the aspirator module includes the primary and secondary aspirators 24, 26. An advantage of the modular design is the ability to control the temperature of the gas sampling system 10 via heating elements associated with the gas sampling system 10 and controlled by control unit 18. This is of particular concern when catalytic heat-flux sensors are utilized since they measure differential changes in temperature.

A control unit 18 compatible with the gas sampling system 10 of the present invention can take a variety of forms as can be appreciated by one of ordinary skill in the art. However, the control unit 18 preferably comprises a signal conditioning circuit for receiving the measurement data from the respective sensors 44, 46, and 48 and for converting it into a desirable format (such as into a digital signal), and a processor for processing the digital signal into an actual measurement value having the appropriate units of measurement. Further, the control unit 18 preferably includes input/output and communication circuitry, a power supply, and an operator interface such as keypad and/or display. In most applications, the processor is programmed with software that controls the operation of the monitoring system 12, such as the operation of solenoid 34 during a blowback operation, the operation of solenoids 64 during calibration, and the operation of solenoid 88 during start-up and under alarm signals. The processor further includes software for performing specific operations on the digital signal to adjust for various parameter, such as changes in the flow rate of the gas sample past the sensor array 38, changes in the temperature of the gas sampling system 10, or numerous other factors as defined by the user who compiles the software.

An example of a suitable control unit 18 for use with the gas sampling system of the present invention is described in U.S. patent application Ser. No. 08/580,710, entitled "Emission Measuring System and Method," invented by Gerald F. Sage and fried on the same day as the present application, the disclosure of which is incorporated herein by reference as if set forth in full.

2. Operation of System a. Sampling of Gas

In operation, the primary aspirator 24 draws a gas sample over line 22 from the exhaust stack 14 via a probe inserted therein. A portion of the gas sample is drawn from the primary aspirator 24 by the secondary aspirator 26. The portion of the gas sample drawn by the secondary aspirator 26 passes over line 36, through sensor array 38, and over line 40 to the secondary aspirator 26. At the sensor array 38, the gas sample in line 36 is equally divided into three gas samples that pass the $NO_x$ sensor 44, the CO sensor 46, and the $O_2$ sensor 48, respectively. The flow rate of the respective gas samples is substantially equal and precisely controlled by the double aspirator design in conjunction with the critical orifices 52.

In addition to the gas sample, the catalytic heat-flux $NO_x$ sensor 44 receives metered amounts of ammonia and makeup air as required for the operation of the $NO_x$ sensor 44. In a like manner, the catalytic heat-flux CO sensor 46 also receives a metered amount of makeup air that is required for the operation of the CO sensor 46.

As the gas samples pass by the respective sensors 44, 46, and 48, the sensors detect the amount of the particular gas of interest that is present in the gas sample. This measurement data is sent to the control unit 18 via cable 20 where it is processed into an actual measurement value. The gas samples delivered to the respective sensors are recombine downstream in line 40 which is plumbed back to exhaust line 42 or exhausted directly into the atmosphere.

b. Calibration

The calibration of the gas sampling system 10 is performed by selectively actuating solenoid valves 64 of gas calibration module 56 in order to provide one of four calibration gases such as: 1) $O_2$ mid span, 2) $CO/O_2$ high span, 3) NO span, or 4) zero gas. At the gas calibration module 56, the calibration valve 58 is used to divert the selected calibration gas to the sampling system (i.e., unit calibration) via line 68 or to an outlet port used to inject calibration gas at the sample probe (i.e., probe calibration) via line 66. The calibration valve 58 can be electrically or manually controlled. In Unit calibration, the secondary sample stream is flooded with the calibration gas at a flow rate controlled by flow restrictor 72. In probe calibration, the sample line at the probe is flooded with calibration gas at a flow rate controlled by a flow restrictor (not shown). The flow residing in the calibration gas inlet fitting on the probe. The appropriate measurements are taken of the calibration gases by the sensors 44, 46, and 48. These measurements are then delivered to the control unit 18 for processing and reporting purposes.

In concluding the detailed description, it should be noted that it will be obvious to those skilled in the art that many variations and modifications may be made to the preferred embodiment without substantially departing from the principles of the current invention. All such variations and modifications are intended to be included herein within the scope of the present invention, as set forth in the following claims. Further, in the claims hereafter, the structures, materials, acts, and equivalence of all means or step plus function elements are intended to include any structures, materials, or acts for performing the functions.

Wherefore, the following is claimed:

1. A gas sampling system for analyzing components of a gas sample extracted from a gas emission stream in an exhaust stack of a process by a probe, comprising:
    a first vacuum means for drawing said gas sample from said gas emission stream in said exhaust stack at a first flow rate;
    a second vacuum means for drawing a portion of said gas sample from said first vacuum means at a second flow rate;
    a sensor array including at least two sensors configured such that a specified quantity of said portion of said gas sample is delivered to each of said sensors at a specified sensor flow rate for each said sensor; and
    a critical orifice downstream of each of said sensors in order to desensitize said sensor flow rate of each said sensor from changes in pressure downstream of each respective said critical orifice.

2. The system of claim 1, further comprising a first pressure sensor configured to measure the upstream pressure of said sensor array and a second pressure sensor configured to measure the downstream pressure of said sensor array for measuring changes in a pressure drop across said sensor array so that adjustments can be made to account for changes in said sensor flow rates as a result of said changes in said pressure drop.

3. The system of claim 1, further comprising a calibration module capable of providing both unit and probe calibration, said module including means for selectively providing calibration gas substantially directly to one of either said sensor array or said probe.

4. The system of claim 1, wherein each said critical orifice includes an upstream filter for removing matter that may hinder operation of said critical orifices.

5. The system of claim 1, wherein said first and second vacuum means are educators.

6. The system of claim 1, wherein said first flow rate is approximately 10 liters per minute and said second flow rate is approximately 3 liters per minute.

7. The system of claim 1, wherein said sensors includes catalytic heat-flux sensors.

8. The system of claim 1, wherein said first flow rate is greater than said second flow rate.

9. The system of claim 1, wherein said sensor array includes a $NO_x$ catalytic heat-flux sensor, a CO catalytic heat-flux sensor, and an $O_2$ zirconia sensor.

10. The system of claim 9, wherein a metered amount of make-up air and ammonia are blended with said gas sample delivered to said $NO_x$ sensor.

11. The system of claim 9, wherein a metered amount of make-up air is blended with said gas sample delivered to said CO sensor.

12. A gas sampling system for analyzing components of a gas sample extracted from a gas emission stream in an exhaust stack of an industrial process by a probe for both continuous emissions and process control monitoring, said system capable of being mounted in an on-stack or off-stack configuration, and comprising:
    a sensor module including an array of sensors, each sensor configured to receive a portion of said gas sample at specified flow rates;
    a calibration module including a calibration valve for selectively delivering calibration gas to one of either said sensor array and said probe; and
    an aspirator module in communication with said sensor module and including a primary aspirator for drawing said gas sample from said exhaust stack at a first flow rate and a secondary aspirator for drawing a portion of said gas sample from said primary aspirator and through said sensor module at a second flow rate.

13. The system of claim 12, wherein said sensor module further includes a critical orifice associated with each said sensor for desensitizing said second flow rate from changes in pressure downstream of said sensor module.

14. The system of claim 12, wherein said first flow rate is approximately 10 liters per minute and said second flow rate is approximately 3 liters per minute.

15. The system of claim 12, wherein said primary and secondary aspirators are educators.

16. A gas sampling system for analyzing components of a gas sample extracted from a gas emission stream in an exhaust stack of an industrial process by a probe for both continuous emissions and process control monitoring said system capable of being mounted in an on-stack or off-stack configuration, comprising:
    a sensor module including an array of sensors, each sensor configured to receive a portion of said gas sample at specified flow rates;
    a calibration module including a calibration valve for selectively delivering calibration gas to one of either said sensor array and said probe;
    an aspirator module in communication with said sensor module and including a primary aspirator for drawing said gas sample from said exhaust stack at a first flow rate and a secondary aspirator for drawing a portion of said gas sample from said primary aspirator and through said sensor module at a second flow rate;
    a pressure differential measurement means for detecting changes in a pressure drop across said sensor module; and
    a critical orifice associated with each said sensor of said sensor module for desensitizing said second flow rate from changes in pressure downstream of said sensor module.

17. A method for extracting a gas sample from a gas stream in an exhaust stack of a process by a probe, comprising the steps of:
    drawing said gas sample from said gas stream in said exhaust stack at a first flow rate;
    drawing a portion of said gas sample at a second flow rate;
    passing said portion of said gas sample to a sensor array including at least two sensors configured such that a specified quantity of said portion of said gas sample is delivered to each of said sensors at a specified sensor flow rate for each said sensor;

desensitizing said sensors from changes in pressure downstream of each said sensor by incorporating a critical orifice downstream of each respective said sensor; and measuring a pressure differential across said sensor array so that changes in said sensor flow rates at each of said sensors can be accounted for in analyzing said gas sample.

* * * * *

UNITED STATES PATENT AND TRADEMARK OFFICE
CERTIFICATE OF CORRECTION

Page 1 of 3

PATENT NO. : 5,627,328
DATED : May 6, 1997
INVENTOR(S) : Sheridan, et. al.

It is certified that error appears in the above-indentified patent and that said Letters Patent is hereby corrected as shown below:

column 1, line 43, delete "frees" and replace with "fines".
column 1, line 60, after "NOx", add a closed parentheses ")".

Delete "army" and replace with "array" at the following locations:

column 3, line 67;

column 4, line 37;

column 5, line 5;

column 5, line 12;

column 6, line 65;

column 7, line 11;

column 7, line 41;

column 8, line 16;

column 10, line 34;

column 11, line 65;

column 12, line 66.

Delete "deliver" and replace with "delivers" at the following locations:

column 4, line 52;

column 4, line 53.

UNITED STATES PATENT AND TRADEMARK OFFICE
CERTIFICATE OF CORRECTION

PATENT NO. : 5,627,328
DATED : May 6, 1997
INVENTOR(S) : Sheridan, et. al.

It is certified that error appears in the above-indentified patent and that said Letters Patent is hereby corrected as shown below:

Column 5, line 7, delete "configure" and replace with "configured".
Column 5, line 24, delete "referenced" and replace with "reference"
Column 5, line 66, delete "form" and replace with "from".
Column 6, lines 34-35, delete the hyphenated word "educators" and replace with "eductors".
Column 6, line 54, delete "effects" and replace with "affect".
Column 6, line 55, delete "effects" and replace with "affects".
Column 6, line 60, after the reference numeral 24, delete the words "as described above".
Column 7, line 27, delete "over".
Column 7, line 31, delete "sensor" and replace with "sensors".
Column 7, line 45, delete "falter" and replace with "filter".
Column 8, line 56, delete "dam" and replace with "data".
Column 9, line 45, delete "preferable" and replace with "preferably".
Column 9, line 50, delete "a" and replace with "an".
Column 10, line 15, delete "parameter" and replace with "parameters".
Column 10, line 24, delete "fried" and replace with "filed".
Column 10, line 54, delete "recombine" and replace with "recombined".
Column 11, line 57, delete "educators" and replace with "eductors".
Column 12, line 33, delete 'educators" and replace with "eductors".

UNITED STATES PATENT AND TRADEMARK OFFICE
CERTIFICATE OF CORRECTION

PATENT NO. : 5,627,328
DATED : May 6, 1997
INVENTOR(S) : Sheridan, et. al.

It is certified that error appears in the above-indentified patent and that said Letters Patent is hereby corrected as shown below:

Column 12, line 18, replace the first "and" with "or" such that said line reads--"said sensor array or said probe; and".
Column 12, line 45, replace "and" with "or" such that said line reads--"said sensor array or said probe;".

Signed and Sealed this

Twenty-third Day of September, 1997

*Attest:*

BRUCE LEHMAN

*Attesting Officer*  *Commissioner of Patents and Trademarks*